(12) United States Patent
Parputc et al.

(10) Patent No.: US 10,384,196 B2
(45) Date of Patent: Aug. 20, 2019

(54) HIGHLY SELECTIVE CATALYST AND METHOD OF ISOMERIZATION OF C4—C7 PARAFFIN HYDROCARBONS

(71) Applicant: Reactive Rectification Technology Ltd., St. Petersburg (RU)

(72) Inventors: Oleg I. Parputc, Kirishy (RU); Oleg V. Giiazov, St. Petersburg (RU); Sergey Yu. Devyatkov, Vologda (RU); Aigiza A. Zinnurova, Arhangelskoe (RU)

(73) Assignee: Kellogg Brown & Root LLC, Houston, TX (US)

( * ) Notice: Subject to any disclaimer, the term of this patent is extended or adjusted under 35 U.S.C. 154(b) by 492 days.

(21) Appl. No.: 14/979,721

(22) Filed: Dec. 28, 2015

(65) Prior Publication Data

US 2016/0185687 A1 Jun. 30, 2016

Related U.S. Application Data

(60) Provisional application No. 62/096,912, filed on Dec. 26, 2014.

(51) Int. Cl.

| | | |
|---|---|---|
| *B01J 21/04* | (2006.01) | |
| *B01J 23/42* | (2006.01) | |
| *B01J 23/44* | (2006.01) | |
| *B01J 23/02* | (2006.01) | |
| *B01J 27/053* | (2006.01) | |
| *C07C 5/27* | (2006.01) | |
| *C10G 45/62* | (2006.01) | |
| *B01J 37/00* | (2006.01) | |
| *B01J 37/02* | (2006.01) | |

(52) U.S. Cl.
CPC ........... *B01J 27/053* (2013.01); *C07C 5/2791* (2013.01); *C10G 45/62* (2013.01); *B01J 37/0009* (2013.01); *B01J 37/0201* (2013.01); *B01J 2523/00* (2013.01); *C07C 2521/04* (2013.01); *C07C 2521/06* (2013.01); *C07C 2523/42* (2013.01); *C07C 2523/44* (2013.01); *C10G 2300/1081* (2013.01)

(58) Field of Classification Search
CPC ........ B01J 27/053; B01J 21/066; B01J 21/04; B01J 23/42; B01J 23/44; B01J 23/02
USPC .................. 502/333, 334, 339, 349; 585/670
See application file for complete search history.

(56) References Cited

U.S. PATENT DOCUMENTS

| | | | |
|---|---|---|---|
| 5,214,017 A | 5/1993 | Angstadt et al. | |
| 5,310,868 A | 5/1994 | Angstadt et al. | |
| 5,494,571 A | 2/1996 | Umansky et al. | |
| 6,037,303 A | 3/2000 | Peratello et al. | |
| 6,080,904 A | 6/2000 | Chang et al. | |
| 6,180,555 B1 | 1/2001 | Szabo et al. | |
| 6,420,305 B1* | 7/2002 | Matsuzawa | B01J 21/066 502/222 |
| 7,022,889 B2 | 4/2006 | Gillespie et al. | |
| 7,026,268 B2* | 4/2006 | Furuta | B01J 23/42 502/217 |
| 7,041,866 B1* | 5/2006 | Gillespie | B01J 27/053 208/111.01 |
| 7,368,626 B2 | 5/2008 | Matsushita | |
| 8,153,548 B2 | 4/2012 | Khurshid et al. | |
| 8,912,110 B2* | 12/2014 | Serban | B01J 23/63 208/134 |
| 9,382,185 B2* | 7/2016 | Held | C07C 45/60 |
| 2005/0027154 A1* | 2/2005 | Vassilakis | B01J 23/63 585/750 |
| 2012/0317872 A1* | 12/2012 | Powell | C10L 5/44 44/307 |

OTHER PUBLICATIONS

M. R. Smith et al., "Skeletal reactions of hydrocarbons on platinum/sulphated zirconia superacid catalysts having an oxidative redispersion stage in their preparation: A polar mechanism of C—C bond scission on platinum affects selectivity." Applied Catalysis A : General 165, pp. 357-370. (Year: 1997).*

Erming Liu et al., "Sulfated fibrous ZrO2/Al2O3 core and shell nanocomposites: A novel strong acid catalyst with hierarchically macro-mesoporous nanostructure." Journal of Molecular Catalysis A: Chemical 353-354, pp. 95-105. (Year: 2012).*

* cited by examiner

*Primary Examiner* — Patricia L. Hailey
(74) *Attorney, Agent, or Firm* — Gary Machetta

(57) ABSTRACT

The invention relates to isomerization catalysts and can be used in the petroleum processing and petrochemical industry. The catalyst contains sulfated zirconium oxide and a binder—aluminum oxide in a ratio of ZrO2/SO4 to Al2O3 from 70 to 30 to 90 to 10, as well as promoter, a group II metal, Ca, in a quantity ranging from 0.01 to 1 wt % of the weight of the catalyst. The catalyst also contains platinum and/or palladium in a quantity ranging from 0.1 to 0.45 wt % of the metal. Isomerization of C4-C7 paraffinic hydrocarbons in the presence of hydrogen at a temperature of 110-200° C., a pressure of 1-5 MPa, a hydrogen:hydrocarbon ratio of 0.5-4, and a feedstock space velocity of 0.5-4 $h^{-1}$ is carried out on a catalyst having the claimed composition. The proposed catalyst offers an enhanced degree of isomerization, improved selectivity of the process, and increased strength of the granules.

7 Claims, No Drawings

HIGHLY SELECTIVE CATALYST AND METHOD OF ISOMERIZATION OF C4—C7 PARAFFIN HYDROCARBONS

RELATED APPLICATIONS

This application claims priority to Provisional Patent Application U.S. 62/096,912 filed on Dec. 26, 2014, which is incorporated herein by reference in its entirety.

FIELD OF THE INVENTION

The invention relates to isomerization catalysts and can be used in the petroleum processing and petrochemical industry. The catalyst contains sulfated zirconium oxide and a binder—aluminum oxide at a ratio of $ZrO2/SO4$ to $Al2O3$ from 70 to 30 to 90 to 10, as well as promoter, a group II metal, Ca, in a quantity ranging from 0.01 to 1 wt % of the weight of the catalyst. The catalyst also contains platinum and/or palladium in a quantity ranging from 0.1 to 0.45 wt % of the metal.

Isomerization of C4-C7 paraffinic hydrocarbons in the presence of hydrogen at a temperature of 110-200° C., a pressure of 1-5 MPa, a hydrogen-to-hydrocarbon ratio of 0.5-4, and a feedstock space velocity of 0.5-4 $h^{-1}$ is carried out on the catalyst having the claimed composition. The proposed catalyst offers an enhanced degree of isomerization, improved selectivity of the process, and increased strength of the catalyst granules.

BACKGROUND OF THE INVENTION

Processes for the isomerization of paraffinic hydrocarbons are used in the petroleum processing and petrochemical industry to increase the octane numbers of gasoline fractions and to obtain individual isomers.

In connection with the introduction of standards that limit the content of oxygenates and aromatic hydrocarbons in motor fuel, isomerizate becomes the principal source of hydrocarbons with high antiknock quality. Processes of isomerization of paraffinic hydrocarbons on heterogeneous acid catalysts are use to obtain the isomerizate. However, many isomerization catalysts promote the formation of C1-C4 gases due to the cracking reaction, which decreases the total yield of C5+ hydrocarbons.

Recently, catalysts based on zirconium oxide have been actively studied. Catalysts based on zirconium oxide, using various oxo-anions as promoters, have been considered in publications U.S. Pat. Nos. 6,180,555 B1, 6,080,904, and 7,368,626 B2. It is also known that the most active catalysts are those based on zirconium oxide, promoted by a compound of sulfur(VI) oxide, for example, U.S. Pat. Nos. 5,494,571 and 6,037,303. In order to reduce the yield of cracking by-products and to prolong the life of the catalyst, a group VIII hydrogenating metal is introduced additionally into catalysts. At the same time, there are examples of catalysts that include in their composition, besides the hydrogenating component, rare earth metals. Lanthanide-series metals, yttrium, and group VIII metals are used as an additional promoter in U.S. Pat. No. 7,022,889. Catalysts based on zirconium oxide, promoted by oxides or hydroxides of group VI, VII, and VIII metals, oxides or hydroxides of group I-B, II-B, III-A, III-B, IV-B, V-A, or VI-A metals, as well as those containing lanthanide-series metals are described in U.S. Pat. Nos. 5,310,868 and 5,214,017.

It is known that a catalyst capable of initiating the isomerization of paraffinic hydrocarbons at low temperatures (including catalysts based on sulfated zirconium oxide) has strong acid centers, where cracking reactions proceed in parallel with isomerization reactions. In case of occurrence of parallel reactions, an important characteristic of the catalyst is its selectivity with respect to the desired end products. Selectivity may be varied by means of process parameters (process pressure, hydrogen-to-hydrocarbon ratio, process temperature, space velocity) or by the introduction of promoters—platinum group metals and/or rare earth metals. It is characteristic that to increase selectivity toward the isomerization reaction it is necessary to carry out the process at increased hydrogen pressure and a low hydrogen-to-hydrocarbon mole ratio; this impairs the economic parameters of the process. On the other hand, the introduction of rare earth metal promoters results in an increased cost of the catalyst.

The publication, U.S. Pat. No. 8,153,548 B2, is the closest to the present invention. Its authors have proposed a catalyst comprised of tungstated zirconium oxide, containing a hydrogenating/dehydrogenating component from the group VIII metals and having in its composition an alkaline component from the group I metals—lithium, sodium, potassium, rubidium, and cesium. However, as is known, tungstated zirconium manifests catalytic activity at temperatures substantially exceeding those for catalysts based on sulfated zirconium, which, according to thermodynamics, decreases the selectivity of the isomerization reaction of paraffinic hydrocarbons.

SUMMARY OF THE INVENTION

This invention describes an improved highly selective isomerization catalyst for C4-C7 paraffins and a method of isomerization of C4-C7 paraffins on the catalyst described. The present invention is based on the discovery that a catalyst promoted by a calcium compound demonstrates high selectivity for branched hydrocarbons and low yield of cracking products.

The broadest embodiment of the invention relates to a catalyst comprised of zirconium oxide with a deposited compound of sulfur, aluminum oxide as a binder, and promoters of platinum and/or palladium and calcium. Here, the compound of sulfur may be any known to a person skilled in the art that, upon thermal activation, is capable of yielding, in combination with zirconium oxide, a solid active acid catalyst. Platinum and/or palladium are introduced into the catalyst by any method known to a person skilled in the art. Calcium is introduced into the catalyst from its water-soluble salt by any method and at any stage. The binder, sulfated zirconium oxide/hydroxide, and the promoters may be combined in any order facilitating the formation of the active catalyst A method of isomerization of hydrocarbons, according to the present invention, consists of the feeding of the hydrogen-hydrocarbon mixture (comprised primarily of C4-C7 paraffins) into a reaction system, containing the catalyst claimed by the authors of the invention, with a hydrocarbon space velocity of 0.5-4 $h^{-1}$. In addition, the hydrogen-to-hydrocarbon ratio ranges from 0.5 to 4. The temperature in the reaction site should be maintained in the range from 110 to 200° C. and the pressure from 1 to 5 MPa. This increases the degree of isomerization, selectivity of the process, and strength of the catalyst granules obtained.

DETAILED DESCRIPTION OF THE PREFERRED EMBODIMENTS

The catalyst, according to this invention, consists of zirconium oxide with a deposited compound of sulfur. In addition the sulfated zirconium oxide, the catalyst consists of aluminum oxide, serving as the binder. The catalyst also contains promoters: a hydrogenating metal, i.e., platinum and/or palladium, and calcium.

Zirconium hydroxide for the catalyst claimed by the authors of the invention can be obtained using techniques known to a person skilled in the art, including precipitation of zirconium hydroxide from its salts, hydrolysis of organic compounds of zirconium, hydrothermal synthesis, etc.

The compound of sulfur on zirconium oxide/hydroxide contains oxygen and is a sulfo group immobilized on the surface of the zirconium oxide/hydroxide. Any means known to persons skilled in the art are used for the deposition of the sulfo group onto zirconium oxide/hydroxide, namely impregnation with sulfuric acid or ammonium sulfate, treatment with hydrogen sulfide, and so on. It is acceptable to use commercially available sulfated zirconium hydroxide. The binder—aluminum oxide—is chosen from among compounds traditional for this art, and is, as a rule, aluminum hydroxide—pseudoboehmite or boehmite, that are capable of forming aluminum oxide with a well-developed specific surface upon calcination. The sulfated zirconium oxide/hydroxide and aluminum hydroxide are mixed together and granulated by any method permitting the production of a support of the requisite geometric form. The support is subjected to drying in air, then to drying at 110-130° C. The support is then calcined at a temperature ranging from 500 to 700° C. and a hydrogenating metal, platinum and/or palladium, is deposited onto the system from a solution of any of their salts (the choice of salt has no influence on this invention) by the method of complete moisture absorption. The catalyst obtained is further subjected to drying at a temperature ranging from 110 to 130° C. and is activated by heat treatment in an air stream at a temperature ranging from 350 to 550° C. Calcium is introduced into the catalyst at any stage and, in addition, may also be found in the crystal lattice of the zirconium.

In the preferred embodiment of the invention, the ratio of sulfated zirconium oxide and aluminum oxide ranges from 7 to 3 up to 9 to 1, calcium is introduced at the stage of mixing of the sulfated zirconium oxide/hydroxide and aluminum hydroxide and is present in a quantity ranging from 0.01 to 1% of the weight of the absolutely dry support. The heat treatment conditions comprise drying at 110-130° C. and calcining in a still atmosphere at temperatures ranging from 500 to 700° C., preferably from 600 to 700° C. The content of the hydrogenating component, platinum and/or palladium, is 0.1-0.45% of the weight of the support. After deposition of the hydrogenating component, the catalyst is dried at 110-130° C. and calcined in an air stream at a temperature ranging from 350 to 550° C.

In the preferred embodiment of the invention, the stage of mixing of the sulfated zirconium oxide/hydroxide and aluminum oxide powders is accompanied by the introduction of calcium from a solution of a salt, nitrate or chloride, and peptization using an inorganic acid—nitric, sulfuric, or their mixture with one another in varied ratio. In the preferred embodiment of the invention, peptization is carried out with a mixture of concentrated nitric and sulfuric acid in a ratio from 1:1 to 4:1 by volume, respectively.

In addition, the authors of this invention unexpectedly discovered that the introduction of calcium into the composition of the catalyst increases the strength of the support granules; as is known by persons skilled in the prior art, this has a positive effect on the useful life of the catalyst and simplifies the loading and unloading of the catalytic units. In addition, the authors were able to establish that the maximal strength of the catalyst is achieved through the introduction of calcium at the stage of mixing of the sulfated zirconium oxide/hydroxide and aluminum hydroxide and peptization of the mixture of powders by nitric or sulfuric acids or by a nitric-sulfuric acid mixture.

A feedstock, containing C4-C7 paraffins is suitable for the isomerization process. The authors of the proposed invention suggest a reaction system for the use of the catalyst that ensures a temperature of 110-200° C., a pressure of 1-5 MPa, a hydrogen-to-hydrocarbon ratio of 0.5-4, and a hydrocarbon feed space velocity of 0.5-4 $h^{-1}$ in the isomerization zone. As the authors of the invention note, a reactor with an immobile catalyst layer, a cascade of reactors with an immobile catalyst layer, as well as a reaction-distillation system with the reactor either internal or external to the column, satisfy these conditions. In addition, the authors allow for the use of both fresh and recycled hydrogen.

The catalyst described in this invention ensures high selectivity with respect to the isomerizate and does not include rare-earth metal promoters.

The following examples serve to illustrate certain specific embodiment of the present invention. They do not limit the claims of the invention.

Example 1

Samples of catalysts were prepared with varied content of the promoter, calcium, and by different peptization methods as shown in table 1. Sulfated zirconium hydroxide manufactured by MEL Chemicals was mixed with boehmite aluminum hydroxide in a 3 to 1 ratio; the slurry was moistened with desalinated water, following which it was subjected to peptization by nitric or sulfuric acid, or their mixture. The introduction of calcium from a solution of its chloride in various quantities followed next. After the introduction of all components, the slurry was stirred for 1 hour, after which the support was formed using a screw extruder into cylinders 1.6 mm in diameter and 5 mm in length. The articles obtained were dried in air, after which they were placed in a temperature-regulated chamber with circulating air and held at a temperature of 120° C. for 5 hours. The support was then calcined in a muffle furnace at 600° C. for 2 hours, cooled to room temperature, and impregnated with a solution of chloroplatinic acid on the basis of 0.3% metallic platinum by weight of the absolutely dry support, after which it was cured in air and was dried again in a temperature-regulated chamber with circulating air at a temperature of 120° C. for 5 hours. Activation in an air stream was the concluding stage: the catalyst was heated to 480° C. and held at the set temperature for 2 hours.

TABLE 1

| Sample number | $Ca^{2+}$ content, wt % | Quantity of conc. $HNO_3$, vol % of the support | Quantity of conc. $H_2SO_4$, vol % of the support |
|---|---|---|---|
| 1 | 0.1 | 4 | 1 |
| 2 | 0.5 | 4 | 1 |
| 3 | 0.8 | 4 | 1 |
| 4 | 0.8 | 2 | 2 |
| 5 | 0.8 | 4 | 0 |
| 6 | 0 | 2 | 0 |

The crush strength of the catalysts was measured according to the standard ASTM D6175-03; the results are shown in table 2.

Example 2—Comparative

A catalyst, designated as sample 7, was prepared according to the U.S. Pat. No. 8,153,548 B2. Ammonium metatungstate in an amount of 0.743 g was dissolved in 3.72 mL of distilled water and applied to 5.73 g of zirconium hydroxide ($ZrO_2$-$xH_2O$). The resulting slurry was heated to 100° C. and held for an hour at this temperature. The resulting slurry was calcined at 780° C. in an air stream and held for 3 hours at this temperature. Then, 1.07 mg of sodium acetate was dissolved in 1.5 mL of distilled water and applied to 3.0 g of tungstated zirconium. Then the slurry was calcined at 450° C. in an air stream for an hour. Chloroplatinic acid in an amount of 56.25 mg from a solution in distilled water was applied to the catalytic slurry, after which the slurry was dried at 100° C. for an hour and calcined at 450° C. for 3 hours in an air stream. The resulting slurry was formed into cylinders, 1.6 mm in diameter and 5 mm in length, by means of a screw extruder. The values of the resulting catalyst are shown in table 2.

Example 3

Samples of catalysts were tested in a pilot flow-through facility with a fixed catalyst layer. A sample, 40 $cm^3$ in volume, was loaded into a flow-through reactor, reduced in a hydrogen stream at a temperature of 180° C. and a pressure of 20 g.a. for 6 hours. The temperature is then decreased to 150° C., the feedstock (99.9% n-hexane) is fed with a hydrocarbon space velocity of 2 $h^{-1}$. The hydrogen-to-hydrocarbon mole ratio is kept at 4. The purity of the hydrogen at inflow into the facility is 99.9999%. The products of the tests were analyzed using a gas chromatograph with a capillary column. The results of the tests are shown in table 2.

TABLE 2

| Sample number | Conversion | Isomerizate yield, % | Strength, N/mm |
|---|---|---|---|
| 1 | 85.5 | 97.5 | 10.1 |
| 2 | 83.2 | 98.1 | 13.2 |
| 3 | 82.7 | 99.7 | 16.1 |
| 4 | 86.6 | 99.4 | 18.9 |
| 5 | 80.3 | 99.8 | 14.5 |
| 6 | 78.8 | 97.1 | 8.8 |
| 7 | 10.3 | 100 | 5.6 |

The results of samples 1-5 illustrate the fact that the introduction of calcium increases selectivity; this is reflected in the increase in isomerizate yield. The crush tests of the samples demonstrate that these samples additionally have increased strength by comparison with sample 6 which does not contain calcium, which moreover demonstrated lower conversion and isomerizate yield. Comparative catalyst sample No. 7 (prototype) demonstrated low strength and an unsatisfactory level of conversion at the temperature of the catalyst tests, which, as is known from prior art, is associated with a relatively low strength of the acid centers on the surface of the tungstated zirconium oxide by comparison with sulfated zirconium oxide.

What is claimed is:

1. An isomerization catalyst for C4-C7 paraffinic hydrocarbons, the catalyst comprising a sulfated zirconium oxide, an inorganic oxide as a binder, a group VIII metal as a hydrogenating component, and a group II metal as a promoter, the catalyst being made at least by mixing powders of a sulfated zirconium hydroxide and an inorganic oxide and/or hydroxide binder, a solution of a group II metal inorganic salt, and a nitric acid and sulfuric acid solution, wherein the content of the group II metal promoter in the isomerization catalyst is greater than 0.5 wt. % and less than 1 wt. %.

2. The catalyst according to claim 1, wherein the group II metal used as the promoter is calcium added in a form of calcium chloride and/or nitrate.

3. The catalyst according to claim 1, wherein an aluminum oxide and/or hydroxide is used as a binder, wherein a ratio of the sulfated zirconium oxide to the aluminum oxide in the isomerization catalyst ranges from 7:3 up to 9:1.

4. The catalyst according to claim 1, wherein platinum and/or palladium in an amount of 0.1-0.45 wt % are used as the group VIII metal.

5. The catalyst according to claim 1, wherein the content of sulfate ions in the zirconium oxide is no less than 5% of a calcined material.

6. The catalyst according to claim 1, wherein the catalyst provides a selectivity to an isomerizate greater than that of a catalyst comprising no group II metal promoter.

7. The catalyst according to claim 1, wherein the catalyst exhibits a strength of catalyst granules greater than that of a catalyst comprising no group II metal promoter.

* * * * *